United States Patent [19]
Bundy

[11] 3,996,267
[45] Dec. 7, 1976

[54] 3-OXO PHENYL-SUBSTITUTED PGF COMPOUNDS
[75] Inventor: Gordon L. Bundy, Portage, Mich.
[73] Assignee: The Upjohn Company, Kalamazoo, Mich.
[22] Filed: Oct. 23, 1975
[21] Appl. No.: 625,241

Related U.S. Application Data

[60] Division of Ser. No. 459,759, April 11, 1974, Pat. No. 3,931,289, which is a continuation of Ser. No. 185,448, Sept. 30, 1971, abandoned, which is a continuation-in-part of Ser. No. 103,338, Dec. 31, 1970, abandoned.

[52] U.S. Cl. .................. 260/473 A; 260/345.7; 260/345.8; 260/520 B
[51] Int. Cl.² ................ C07C 5/22; C07C 69/76
[58] Field of Search ......... 260/473 A, 520 B, 345.8

[56] References Cited
UNITED STATES PATENTS 3,864,387  2/1975  Nelson ........................ 260/473 A
3,879,438  4/1975  Crabbe et al. ................ 260/473 A Primary Examiner—Paul J. Killos
Attorney, Agent, or Firm—Morris L. Nielsen

[57] ABSTRACT

This invention is a group of 3-oxa and 4-oxa phenyl-substituted PGE type, PGF type, PGA type and PGB type compounds, and processes for making those. These compounds are useful for a variety of pharmacological purposes, including anti-ulcer, inhibition of platelet aggregation, increase of nasal patency, labor inducement at term, and wound healing.

37 Claims, No Drawings

3-OXO PHENYL-SUBSTITUTED PGF COMPOUNDS

CROSS REFERENCE TO RELATED APPLICATIONS

This is a division, of application Ser. No. 459,759, filed Apr. 11, 1974 now U.S. Pat. No. 3,931,289 which is a continuation of my copending application Ser. No. 185,448, filed Sept. 30, 1971, now abandoned which was a continuation-in-part of my copending application Ser. No. 103,338 filed Dec. 31, 1970, and now abandoned.

DESCRIPTION OF THE INVENTION

This invention relates to novel compositions of matter, to novel methods for producing them, and to novel chemical intermediates useful in those processes. Particularly, this invention relates to certain novel analogs of prostaglandins $E_1$, $E_2$, $F_{1\alpha}$, $F_{1\beta}$, $F_{2\alpha}$, $F_{2\beta}$, $A_1$, $A_2$, $B_1$, $B_2$, and the dihydro derivatives of the $PG_1$ compounds. These novel analogs each have an oxa oxygen (—O—) in place of the methylene (—CH$_2$—) moiety at the three-position or at the 4-position of the prostanoic acid structure and also have a benzene ring as part of the C–13 to C–20 chain of the prostanoic acid.

The essential material for this application, including the background of the invention, the disclosure of the invention, and the description of the preferred embodiments, including Preparations and Examples, is incorporated by reference from U.S. Pat. No. 3,931,289, columns 1-101, inclusive, under the provisions of M.P.E.P. 608.01(p).

The following formulas represent the novel 3-oxa phenyl-substituted prostaglandin analogs of this invention:

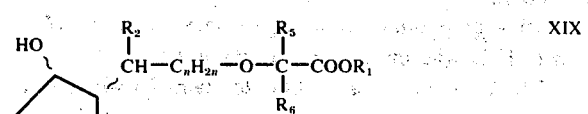

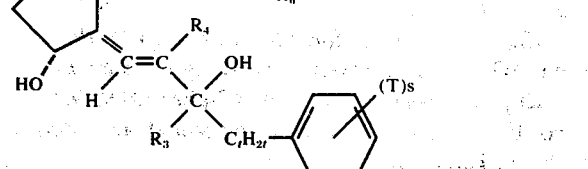

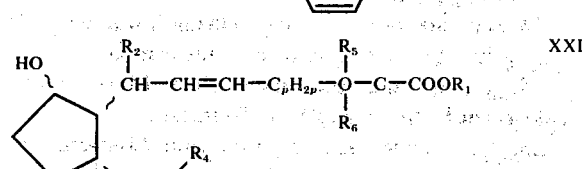

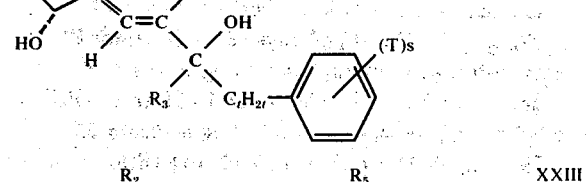

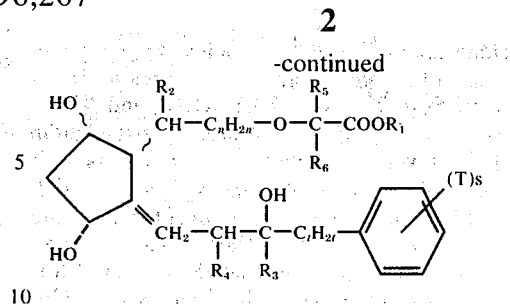

Formulas XIX, XXI, XXIII, and XXV represent 3-oxa phenyl-substituted compounds of the PGF type.

In those formulas $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one to 3 chloro or alkyl of one to 4 carbon atoms, inclusive, or ethyl substituted in the $\beta$-position with 3 chloro, 2 or 3 bromo, or 1, 2, or 3 iodo. $R_2$, $R_3$, $R_4$, $R_5$, $R_6$, $R_7$, and $R_8$ are hydrogen or alkyl of one to 4 carbon atoms, inclusive. The divalent moiety —$C_nH_{2n}$— represents alkylene of one to 10 carbon atoms, inclusive, with one to 5 carbon atoms, inclusive, between —$CHR_2$— and —O—. The divalent moiety —$C_mH_{2m}$— represents alkylene of one to 9 carbon atoms, inclusive, with 1 to 4 carbon atoms, inclusive, between —$CHR_2$— and —O—. The divalent moiety —$C_pH_{2p}$— represents alkylene of one to 8 carbon atoms, inclusive, with one, 2, or 3 carbon atoms between —CH=CH— or —C≡C— and —O—. The divalent moiety —$C_qH_{2q}$— represents alkylene of one to 7 carbon atoms, inclusive, with 1 or 2 carbon atoms between —CH=CH— or —C≡C— and —O—. The moiety —$C_tH_{2t}$— represents a valence bond, i.e., wherein t is zero, or alkylene of one to 10 carbon atoms, inclusive, i.e., wherein t is one to 10, substituted with zero, one, or 2 fluoro, with one to 7 carbon atoms, inclusive, between —$CR_3OH$— and the ring. When one or 2 fluoro are present as substituents of —$C_tH_{2t}$—, that moiety will contain 2t-1 or 2t-2 hydrogen atoms, respectively, rather than 2t hydrogen atoms. The symbol T represents alkyl of one to 4 carbon atoms, inclusive, fluoro, chloro, trifluoromethyl, or —$OR_9$, wherein $R_9$ is hydrogen, alkyl of one to 4 carbon atoms inclusive, or tetrahydropyranyl. The symbol s represents zero, one, 2 or 3. Regarding the combination (T)$_s$ attached to the phenyl ring, no more than two T are other than alkyl. Except for that proviso, when two or three T are present as substituents, they are the same or different.

The wavy line ~ in formulas XIX, XXI, XXIII, and XXV indicates attachment of the group to the ring in alpha or beta configuration. In the case of the compounds of formulas XIX, XXI, XXIII, and XXV, also, there are two wavy lines, and those formulas encompass compounds wherein the configurations of the hydroxy and the carboxyl-terminated moieties are, respectively, $\alpha,\alpha$, $\alpha,\beta$, $\beta,\alpha$, and $\beta,\beta$.

Formulas XIX, XXI, XXIII, and XXV include lower alkanoates, and also pharmacologically acceptable salts when $R_1$ is hydrogen.

Also included in Formulas XIX, XXI, XXIII, and XXV are separate isomers wherein the side chain hydroxy is in S or R (epi) configuration.

Included in Formula XXI, are both the cis and the trans compounds with respect to the carbon-carbon double bond in the carboxy terminated side chain. In all of the compounds containing —CH=$CR_4$—, that carbon-carbon double bond is in trans configuration, and the chain containing R₄ is attached to the cyclopentane ring in beta configuration in compounds encompassed by Formulas XIX, XXI, XXIII, and XXV.

The novel 3-oxa phenyl-substituted prostaglandin analogs of this invention include racemic compounds and both optically active enantiomeric forms thereof. As discussed hereinabove, two structural formulas are required to define accurately these racemic compounds. For convenience, only a single structural formula is used, for example Formulas XIX, XXI, XXIII, and XXV, to define the racemic form and both enantiomeric forms of each group of novel prostoglandin analogs. Each formula is, however, to be construed as including said racemic forms and both of said optically active enantiomeric forms.

I claim:
1. A compound of the formula:

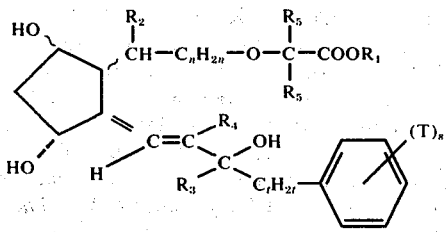

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, and $R_6$ are hydrogen or alkyl of one to 4 carbon atoms, inclusive; wherein $C_nH_{2n}$ is alkylene of one to 10 carbon atoms, inclusive, with one to 5 carbon atoms, inclusive, between —CH-$R_2$— and —O—; wherein $C_tH_{2t}$ represents (1) a valence bond or (2) alkylene of one to 10 carbon atoms, inclusive, substituted with zero, one, or 2 fluoro, with 1 to 7 carbon atoms, inclusive, between —CR₃OH— and the ring; wherein T is alkyl of one to 4 carbon atoms, inclusive, fluoro, chloro, trifluoromethyl, or —OR₉, wherein R₉ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when R₁ is hydrogen.

2. A compound according to claim 1 wherein

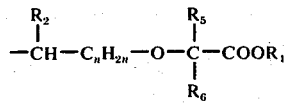

—(CH₂)₄—O—CH₂COOR₁,
wherein R₁ is as defined in claim 1.

3. A compound according to claim 2 wherein ~OH is attached to the ring in alpha configuration.

4. A compound according to claim 3 wherein $C_tH_{2t}$ is straight chain alkylene of one to 4 carbon atoms with or without a fluoro or alkyl substituent on the carbon atom adjacent to the hydroxy-substituted carbon atom.

5. A compound according to claim 4 wherein the side chain hydroxy is in S configuration.

6. A compound according to claim 5 wherein R₄ is hydrogen.

7. A compound according to claim 6 wherein R₃ is hydrogen.

8. A compound according to claim 7 wherein $C_tH_{2t}$ is $(CH_2)_d$ wherein d is one, 2, 3, or 4.

9. A compound according to claim 8 wherein d is 2.

10. 3-Oxa-17-phenyl-18,19,20-trinor-PGF₁α, a compound according to claim 9

11. 3-Oxa-17-phenyl-18,19,20-trinor-PGF₁α, ethyl ester, a compound according to claim 9.

12. A compound according to claim 6 wherein R₃ is methyl.

13. A compound according to claim 12 wherein $C_tH_{2t}$ is $(CH_2)_d$ wherein d is one, 2, 3, or 4.

14. A compound according to claim 13 wherein d is 2.

15. 3-Oxa-15-methyl-17-phenyl-18,19,20-trinor-PGF₁α, a compound according to claim 14.

16. 3-Oxa-15-methyl-17-phenyl-18,19,20-trinor-PGF₁α, ethyl ester, a compound according to claim 14.

17. A compound according to claim 4 wherein the side chain hydroxy is in R (epi) configuration.

18. A compound according to claim 17 wherein R₄ is hydrogen.

19. A compound according to claim 18 wherein R₃ is methyl.

20. A compound according to claim 19 wherein $C_tH_{2t}$ is $(CH_2)_d$ wherein d is one, 2, 3, or 4.

21. A compound according to claim 20 wherein d is 2.

22. 15-Epi-3-oxa-15-methyl-17-phenyl-18,19,20-trinor-PGF₁α, a compound according to claim 21.

23. 15-Epi-3-oxa-15-methyl-17-phenyl-18,19,20-trinor-PGF₁α, ethyl ester, a compound according to claim 21.

24. A compound according to claim 2 wherein ~OH is attached to the ring in beta configuration.

25. A compound according to claim 24 wherein the side chain hydroxy is in S configuration.

26. A compound according to claim 24 wherein the side chain hydroxy is in R (epi) configuration.

27. dl-3-Oxa-17-phenyl-18,19,20-trinor-PGF₁α ethyl ester, a compound according to claim 9.

28. dl-3-Oxa-17-phenyl-18,19,20-trinor-PGF₁β ethyl ester, a compound according to claim 25.

29. dl-15-Epi-3-oxa-17-phenyl-18,19,20-trinor-PGF₁α ethyl ester, a compound according to claim 18.

30. dl-15-Epi-3-oxa-17-phenyl-18,19,20-trinor-PGF₁β ethyl ester, a compound according to claim 26.

31. dl-3-Oxa-15-methyl-17-phenyl-18,19,20-trinor-PGF₁α ethyl ester, a compound according to claim 14.

32. A compound of the formula:

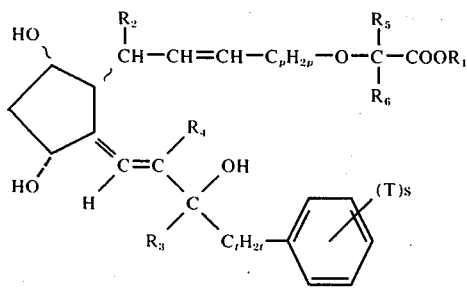

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3chloro, 2 or 3 bromo, or 1, 2, or 3 iodo; wherein $R_2$, $R_3$, $R_4$, $R_5$, and $R_6$ are hydrogen or alkyl of one to 4 carbon atoms, inclusive; wherein $C_pH_{2p}$ is alkylene of one to 8 carbon atoms, inclusive, with one, 2, or 3 carbon atoms between —CH=CH— and —O—; wherein $C_tH_{2t}$ represents (1) a valance bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or -OR$_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and two pharmacologically acceptable salts thereof when $R_1$ is hydrogen.

33. A compound according to claim 32 wherein

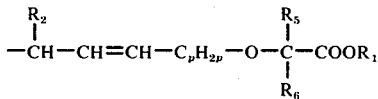

is $-CH_2-CH=CH-CH_2-O-CH_2-COOR_1$, wherein $R_1$ is as defined in claim 11.

34. A compound of the formula:

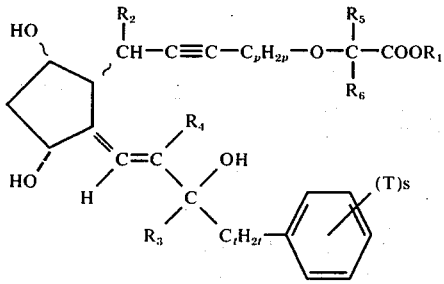

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, and $R_6$ are hydrogen or alkyl of one to 4 carbon atoms, inclusive; wherein $C_pH_{2p}$ is alkylene of one to 8 carbon atoms, inclusive, with one, 2, or 3 carbon atoms between —C C— and —O—; wherein $C_tH_{2t}$ represents (1) a valence bond or (2) alkylene of one to 10 carbon atoms, inclusive, substituted with zero, one, or 2 fluoro, with 1 to 7 carbon atoms, inclusive, between —CR$_3$OH— and the ring; wherein T is alkyl of one to 4 carbon atoms, inclusive, fluoro, chloro, trifluoromethyl, or —OR$_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

35. A compound according to claim 34 wherein

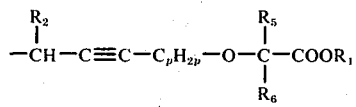

is

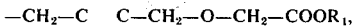

$-CH_2-C \quad C-CH_2-O-CH_2-COOR_1$, wherein $R_1$ is as defined in claim 13.

36. A compound of the formula:

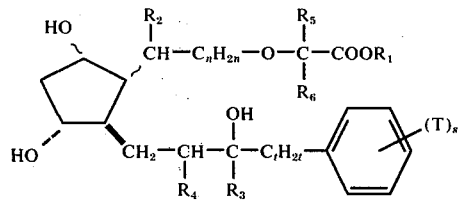

wherein $R_1$ is hydrogen, alkyl of one to 8 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; wherein $R_2$, $R_3$, $R_4$, $R_5$, and $R_6$ are hydrogen or alkyl of one to 4 carbon atoms, inclusive; wherein $C_nH_{2n}$ is alkylene of one to 10 carbon atoms, inclusive, with one to 5 carbon atoms, inclusive, between —CHR$_2$— and —O—; wherein $C_tH_{2t}$ represents (1) a valence bond or (2) alkylene of one to 10 carbon atoms, inclusive, substituted with zero, one, or 2 fluoro, with one to 7 carbon atoms, inclusive, between —CR$_3$OH— and the ring; wherein T is alkyl of one to 4 carbon atoms, inclusive, fluoro, chloro, trifluoromethyl, or —OR$_9$, wherein $R_9$ is hydrogen, alkyl of one to 4 carbon atoms, inclusive, or tetrahydropyranyl, and s is zero, one, 2, or 3, with the proviso that no more than two T are other than alkyl; and wherein ~ indicates attachment of the group to the ring in alpha or beta configuration; including the lower alkanoates thereof, and the pharmacologically acceptable salts thereof when $R_1$ is hydrogen.

37. A compound according to claim 36 wherein

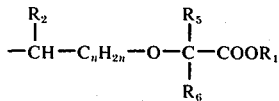

is

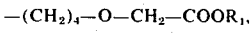

$-(CH_2)_4-O-CH_2-COOR_1$, wherein $R_1$ is as defined in claim 15.

* * * * *

UNITED STATES PATENT OFFICE
CERTIFICATE OF CORRECTION

Patent No. 3,996,267　　　　　　　Dated December 7, 1976

Inventor(s)　　Gordon L. Bundy

It is certified that error appears in the above-identified patent and that said Letters Patent are hereby corrected as shown below:

Column 3, line 24, " 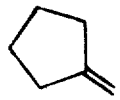 " should read -- 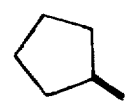 --;

line 58, claim 2, " " should read -- is --.  Column 5, line 5,
" 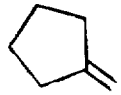 " should read -- 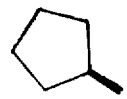 --; line 22, "-C C-"

should read -- -C≡C- --; line 34, "two" should read -- the --;
line 53, " 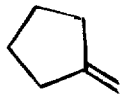 " should read -- 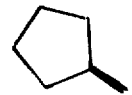 --.

Signed and Sealed this

Sixth Day of September 1977

[SEAL]

Attest:

RUTH C. MASON　　　　　　LUTRELLE F. PARKER
*Attesting Officer*　　　　*Acting Commissioner of Patents and Trademarks*